United States Patent [19]

Kaderbhai

[11] Patent Number: 5,962,222
[45] Date of Patent: *Oct. 5, 1999

[54] PROTEIN FUSIONS FOR THE TRANSLOCATION OF APO-PROTEIN INTO THE PERIPLASMIC SPACE

[76] Inventor: Mustak Ali Kaderbhai, Sunny Hill, Bryn Hendre, Waun Fawr, Aberystwyth Dyfed, United Kingdom, SY23 3PP

[ * ] Notice: This patent issued on a continued prosecution application filed under 37 CFR 1.53(d), and is subject to the twenty year patent term provisions of 35 U.S.C. 154(a)(2).

[21] Appl. No.: 08/495,500

[22] PCT Filed: Jan. 27, 1994

[86] PCT No.: PCT/GB94/00161

§ 371 Date: Nov. 13, 1995

§ 102(e) Date: Nov. 13, 1995

[87] PCT Pub. No.: WO94/17191

PCT Pub. Date: Aug. 4, 1994

[30] Foreign Application Priority Data

Jan. 27, 1993 [GB] United Kingdom .................. 9301553

[51] Int. Cl.[6] .............................. C12Q 1/68; C12P 21/06; C07H 17/00
[52] U.S. Cl. ............................ 435/6; 435/69.1; 435/325; 435/320.1; 536/23.1
[58] Field of Search .......................... 536/23.1; 435/69.1, 435/69.8, 320.1, 325, 71.1, 6, 7.2

[56] References Cited

FOREIGN PATENT DOCUMENTS

0121352  10/1984  European Pat. Off. .

OTHER PUBLICATIONS

Gallagher et al. 1992 Appl Microbiol Biotechnol 38:77–83.
Page et al 1990 Mol. Microbiol. 4(7) 1181–1192.
Stader et al 1990 Methods in Enzymology 185: 166–186.
M. Takahara et al., "Secretion of Human Superoxide Dismutase in *Escherichia coli*", *Biotechnology*, vol. 6, No. 2, pp. 195–198, (1988).
A. Karim et al., "Efficient Bacterial Export of a Eukaryotic Cytoplasmic Cytochrome", *Bio/Technology*, vol. 11, No. 5, pp. 612–618, (1993).
V. Harding et al., "Processing of chimeric mammalian cytochrome $b_5$ precursors in *Escherichia coli*: reaction specificity of signal peptidase and identification of an aminopeptidase in post–translocation processing", *Biochemical Journal*, vol. 293, No. 3, pp. 751–756, (1993).

*Primary Examiner*—Karen Cochrane Carlson

[57] ABSTRACT

A method of protein synthesis which comprises providing a genetic unit comprising a nucleotide sequence coding for a pre-form apo-protein. The pre-form apo-protein is synthesized in a cytoplasmic region of a cell and translocated to the periplasmic region of the cell for conversion to a corresponding holo-protein.

31 Claims, 14 Drawing Sheets

SEQ ID NO 1

*phoA* promoter
-35 Pribnow box
GTCAGTAAAA AGTTAATCTT TTCAACAGCT GTCATAA<u>AGT TGTCA</u>CGGCC -10 Pribnow box
S/D
GAGACT<u>TATA</u> <u>GT</u>CGCTTTGT TTTTATTTTT TAATGTATTT GTACATGGAG

AAAATAAA ss-21
3056
GTG AAA CAA AGC ACT ATT GCA CTG GCA CTC TTA CCG TTA CTG TTT ACC
Met Lys Gln Ser Thr Ile Ala Leu Ala Leu Leu Pro Leu Leu Phe Thr ss-1  AP+1  $b_5$+1
CCT GTG ACA AAA GCC CGG ATG GCT GAA CAA AGC GAC AAA GAC GTC AAA
Pro Val Thr Lys Ala Arg MET Ala Glu Gln Ser Asp Lys Asp Val Lys

TAC TAC ACT CTG GAA GAA ATC CAA AAA CAC AAA GAC TCG AAG TCG ACG
Tyr Tyr Thr Leu Glu Glu Ile Gln Lys His Lys Asp Ser Lys Ser Thr

TGG GTG ATC CTG CAC CAT AAA GTA TAC GAC CTA ACT AAA TTC CTC GAA
Trp Val Ile Leu His His Lys Val Tyr Asp Leu Thr Lys Phe Leu Glu

GAG CAC CCC GGG GGC GAA GAA GTC CTG AGA GAA CAG GCC GGC GGT GAC
Glu His Pro Gly Gly Glu Glu Val Leu Arg Glu Gln Ala Gly Gly Asp

GCG ACT GAA AAC TTC GAA GAC GTT GGC CAT AGT ACC GAC GCT CGA GAA
Ala Thr Glu Asn Phe Glu Asp Val Gly His Ser Thr Asp Ala Arg Glu

CTG TCG AAA ACG TAC ATC ATC GGT GAG CTG CAC CCG GAC GAT CGT TCT
Leu Ser Lys Thr Tyr Ile Ile Gly Glu Leu His Pro Asp Asp Arg Ser

AAA ATC GCG AAA CCG TCC GAA ACT CTG TAA TGA GAATTCGATA TCAAGCTT
Lys Ile Ala Lys Pro Ser Glu Thr Leu End End

\*********End of data file******************

FIG. 4

SEQ ID NO 2
pSEC-CYT; circular plasmid
1 to 3853 bps.
396-454, polylinker site
2948-2962, *pho* promoter
2996-3001, Shine/Dalgarno sequence
3009-3074, alkaline phosphatase signal sequence (21 residue + 1 $^{AP}$)
3075-3374, soluble core of cytochrome b5
3375-3482, 'tail' of cytochrome b5
Note: Sequence is uncertain between 2700 and 2900 bp.

```
            10         20         30         40         50
TCGCGCGTTT CGGTGATGAC GGTGAAAACC TCTGACACAT GCAGCTCCCG
                                                       100
GAGACGGTCA CAGCTTGTCT GTAAGCGGAT GCCGGGAGCA GACAAGCCCG
                                                       150
TCAGGGCGCG TCAGCGGGTG TTGGCGGGTG TCGGGGCTGG CTTAACTATG
                                                       200
CGGCATCAGA GCAGATTGTA CTGAGAGTGC ACCATATGCG GTGTGAAATA
                                                       250
CCGCACAGAT GCGTAAGGAG AAAATACCGC ATCAGGCGCC ATTCGCCATT
                                                       300
CAGGCTGCGC AACTGTTGGG AAGGGCGATC GGTGCGGGCC TCTTCGCTAT
                                                       350
TACGCCAGCT GGCGAAAGGG GGATGTGCTG CAAGGCGATT AAGTTGGGTA
                                                       400
ACGCCAGGGT TTTCCCAGTC ACGACGTTGT AAAACGACGG CCAGTGAATT
                                                       450
CGAGCTCGGT ACCCGGGGAT CCTCTAGAGT CGACCTGCAG GCATGCAAGC
                                                       500
TTGGCGTAAT CATGGTCATA GCTGTTTCCT GTGTGAAATT GTTATCCGCT
                                                       550
CACAATTCCA CACAACATAC GAGCCGGAAG CATAAAGTGT AAAGCCTGGG
                                                       600
GTGCCTAATG AGTGAGCTAA CTCACATTAA TTGCGTTGCG CTCACTGCCC
                                                       650
GCTTTCCAGT CGGGAAACCT GTCGTGCCAG CTGCATTAAT GAATCGGCCA
                                                       700
ACGCGCGGGG AGAGGCGGTT TGCGTATTGG GCGCTCTTCC GCTTCCTCGC
                                                       750
TCACTGACTC GCTGCGCTCG GTCGTTCGGC TGCGGCGAGC GGTATCAGCT
                                                       800
CACTCAAAGG CGGTAATACG GTTATCCACA GAATCAGGGG ATAACGCAGG
                                                       850
```

FIG. 5

```
AAAGAACATG TGAGCAAAAG GCCAGCAAAA GGCCAGGAACCGTAAAAAGG
                                                    900
CCGCGTTGCT GGCGTTTTTC CATAGGCTCC GCCCCCCTGA CGAGCATCAC
                                                    950
AAAAATCGAC GCTCAAGTCA GAGGTGGCGA AACCCGACAG GACTATAAAG
                                                   1000
ATACCAGGCG TTTCCCCCTG GAAGCTCCCT CGTGCGCTCT CCTGTTCCGA
                                                   1050
CCCTGCCGCT TACCGGATAC CTGTCCGCCT TCTCCCTTC GGGAAGCGTG
                                                   1100
GCGCTTTCTC AATGCTCACG CTGTAGGTAT CTCAGTTCGG TGTAGGTCGT
                                                   1150
TCGCTCCAAG CTGGGCTGTG TGCACGAACC CCCCGTTCAG CCCGACCGCT
                                                   1200
GCGCCTTATC CGGTAACTAT CGTCTTGAGT CCAACCCGGT AAGACACGAC
                                                   1250
TTATCGCCAC TGGCAGCAGC CACTGGTAAC AGGATTAGCA GAGCGAGGTA
                                                   1300
TGTAGGCGGT GCTACAGAGT TCTTGAAGTG GTGGCCTAAC TACGGCTACA
                                                   1350
CTAGAAGGAC AGTATTTGGT ATCTGCGCTC TGCTGAAGCC AGTTACCTTC
                                                   1400
GGAAAAAGAG TTGGTAGCTC TTGATCCGGC AAACAAACCA CCGCTGGTAG
                                                   1450
CGGTGGTTTT TTTGTTTGCA AGCAGCAGAT TACGCGCAGA AAAAAGGAT
                                                   1500
CTCAAGAAGA TCCTTTGATC TTTTCTACGG GGTCTGACGC TCAGTGGAAC
                                                   1550
GAAAACTCAC GTTAAGGGAT TTTGGTCATG AGATTATCAA AAAGGATCTT
                                                   1600
CACCTAGATC CTTTTAAATT AAAAATGAAG TTTTAAATCA ATCTAAAGTA
                                                   1650
TATATGAGTA AACTTGGTCT GACAGTTACC AATGCTTAAT CAGTGAGGCA
                                                   1700
CCTATCTCAG CGATCTGTCT ATTTCGTTCA TCCATAGTTG CCTGACTCCC
                                                   1750
CGTCGTGTAG ATAACTACGA TACGGGAGGG CTTACCATCT GGCCCCAGTG
                                                   1800
CTGCAATGAT ACCGCGAGAC CCACGCTCAC CGGCTCCAGA TTTATCAGCA
                                                   1850
ATAAACCAGC CAGCCGGAAG GGCCGAGCGC AGAAGTGGTC CTGCAACTTT
                                                   1900
ATCCGCCTCC ATCCAGTCTA TTAATTGTTG CCGGGAAGCT AGAGTAAGTA
                                                   1950
GTTCGCCAGT TAATAGTTTG CGCAACGTTG TTGCCATTGC TACAGGCATC
                                                   2000
```

FIG. 5 Cont.

```
GTGGTGTCAC GCTCGTCGTT TGGTATGGCT TCATTCAGCT CCGGTTCCCA
                                                      2050
ACGATCAAGG CGAGTTACAT GATCCCCCAT GTTGTGCAAA AAAGCGGTTA
                                                      2100
GCTCCTTCGG TCCTCCGATC GTTGTCAGAA GTAAGTTGGC CGCAGTGTTA
                                                      2150
TCACTCATGG TTATGGCAGC ACTGCATAAT TCTCTTACTG TCATGCCATC
                                                      2200
CGTAAGATGC TTTTCTGTGA CTGGTGAGTA CTCAACCAAG TCATTCTGAG
                                                      2250
AATAGTGTAT GCGGCGACCG AGTTGCTCTT GCCCGGCGTC AATACGGGAT
                                                      2300
AATACCGCGC CACATAGCAG AACTTTAAAA GTGCTCATCA TTGGAAAACG
                                                      2350
TTCTTCGGGG CGAAAACTCT CAAGGATCTT ACCGCTGTTG AGATCCAGTT
                                                      2400
CGATGTAACC CACTCGTGCA CCCAACTGAT CTTCAGCATC TTTTACTTTC
                                                      2450
ACCAGCGTTT CTGGGTGAGC AAAAACAGGA AGGCAAAATG CCGCAAAAAA
                                                      2500
GGGAATAAGG GCGACACGGA AATGTTGAAT ACTCATACTC TTCCTTTTTC
                                                      2550
AATATTATTG AAGCATTTAT CAGGGTTATT GTCTCATGAG CGGATACATA
                                                      2600
TTTGAATGTA TTTAGAAAAA TAAACAAATA GGGGTTCCGC GCACATTTCC
                                                      2650
CCGAAAAGTG CCACCTGACG TCTAAGAAAC CATTATTATC ATGACATTAA
                                                      2700
CCTATAAAAA TAGGCGTATC ACGAGGCCCT TCGTCTTCA AGAATTCTCA
                                                      2750
TGTTTGACAG CTTATCATCG ATAAGCTAGC TTTGGAGATT ATCGTCACTG
                                                      2800
CAATGCTTCG CAATATGGCG CAAAATGACC AACAGCGGTT GATTGATCAG
                                                      2850
GTAGAGGGGG CGCTGTACGA GGTAAAGCCC GATGCCAGCA TTCCTGACGA
                                                      2900
CGATACGGAG CTGCTGCGCG ATTACGTAAA GAAGTTATTG AAGCATCCTC
                                                      2950
GTCAGTAAAA AGTTAATCTT TTCAACAGCT GTCATAA<u>AGT TGTCA</u>CGGCC
                                                      3000
GAGACT<u>TATA</u> GTCGCTTTGT TTTATTTTT TAATGTATTT GTACATGGAG
           3008
AAAATAAA
                                                      3056
GTG AAA CAA AGC ACT ATT GCA CTG GCA CTC TTA CCG TTA CTG TTT ACC
Met Lys Gln Ser Thr Ile Ala Leu Ala Leu Leu Pro Leu Leu Phe Thr
```

FIG. 5 Cont.

```
                                                                    3104
CCT GTG ACA AAA GCC CGG ATG GCT GAA CAA AGC GAC AAA GAC GTC AAA
Pro Val Thr Lys Ala Arg MET Ala Glu Gln Ser Asp Lys Asp Val Lys
                                                                    3152
TAC TAC ACT CTG GAA GAA ATC CAA AAA CAC AAA GAC TCG AAG TCG ACG
Tyr Tyr Thr Leu Glu Glu Ile Gln Lys His Lys Asp Ser Lys Ser Thr
                                                                    3200
TGG GTG ATC CTG CAC CAT AAA GTA TAC GAC CTA ACT AAA TTC CTC GAA
Trp Val Ile Leu His His Lys Val Tyr Asp Leu Thr Lys Phe Leu Glu
                                                                    3248
GAG CAC CCC GGG GGC GAA GAA GTC CTG AGA GAA CAG GCC GGC GGT GAC
Glu His Pro Gly Gly Glu Glu Val Leu Arg Glu Gln Ala Gly Gly Asp
                                                                    3296
GCG ACT GAA AAC TTC GAA GAC GTT GGC CAT AGT ACC GAC GCT CGA GAA
Ala Thr Glu Asn Phe Glu Asp Val Gly His Ser Thr Asp Ala Arg Glu
                                                                    3344
CTG TCG AAA ACG TAC ATC ATC GGT GAG CTG CAC CCG GAC GAT CGT TCT
Leu Ser Lys Thr Tyr Ile Ile Gly Glu Leu His Pro Asp Asp Arg Ser
                                                                    3392
AAA ATC GCG AAA CCG TCC GAA ACT CTG ATC ACT ACC GTT GAA TCG AAC
Lys Ile Ala Lys Pro Ser Glu Thr Leu Ile Thr Thr Val Glu Ser Asn
                                                                    3440
TCT AGT TGG TGG ACT AAC TGG GTT ATC CCT GCG ATC TCT GCT CTG GTT
Ser Ser Trp Trp Thr Asn Trp Val Ile Pro Ala Ile Ser Ala Leu Val
                                                                    3482
GTA GCG CTG ATG TAC CGT CTG TAC ATG GCT GAA GAT TAA TGA
Val Ala Leu MET Tyr Arg Leu Tyr MET Ala Glu Asp End End
                           3500
GAATTCGATA TCAAGCTT
                                                                    3550
TAGTTCGTCA AGGCTTGGCT AAAGTTGCTT ATGTTTACAA ACCTAACAAT
                                                                    3600
ACATATGAAC AACATTTAAG AAAAAGTGAA GCACAAGCGA AAAAGAGAA
                                                                    3650
ATTAAATATT TGGAGCGAAG ACAACGCTGA TTCAGGTCAA TAATGCTCAT
                                                                    3700
TGTAAAAGTG TCACTGCTGC TAGTGGCACT TTTATAATTT TTAGATCCTC
                                                                    3750
TACGCCGGAC GCATCGTGGC CGGCATCACC GGCGCCACAG GTGCGGTTGC
                                                                    3800
TGGCGCCTAT ATCGCCGACA TCACCGATGG GGAAGATCGG GCTCGCCACT
                                                                    3850
TCGGGCTCAT GAGCGCTTGT TTCGGCGTGG GTATGGTGGC AGGCCCTTTC
     3853
GTC **********End of data file********************
```

FIG. 5 Cont.

SEQ ID NO 3                                  phoA promoter
                                              -35 Pribnow box
GTCAGTAAAA AGTTAATCTT TTCAACAGCT GTCATAA<u>AGT TGTCA</u>CGGCC -10 Pribnow box                                              S/D
GAGACT<u>TATA GT</u>CGCTTTGT TTTTATTTTT TAATGTATTT GTACATGGAG

AAAATAAA

SS-21                                                        3056
GTG AAA CAA AGC ACT ATT GCA CTG GCA CTC TTA CCG TTA CTG TTT ACC
Met Lys Gln Ser Thr Ile Ala Leu Ala Leu Leu Pro Leu Leu Phe Thr

SS-1 AP+1                        $b_5$+1
CCT GTG ACA AAA GCC CGG ATC CCC CGG GCT GCA GAT GGC TGA A CAA AGC
Pro Val Thr Lys Ala Arg Ile Pro Arg Ala Ala   Asp Gly End
Reading frame of cytochrome b5
                                                Met Ala Glu    Gln Ser GAC AAA GAC GTC AAA
Asp Lys Asp Val Lys TAC TAC ACT CTG GAA GAA ATC CAA AAA CAC AAA GAC TCG AAG TCG ACG
Tyr Tyr Thr Leu Glu Glu Ile Gln Lys His Lys Asp Ser Lys Ser Thr TGG GTG ATC CTG CAC CAT AAA GTA TAC GAC CTA ACT AAA TTC CTC GAA
Trp Val Ile Leu His His Lys Val Tyr Asp Leu Thr Lys Phe Leu Glu GAG CAC CCC GGG GGC GAA GAA GTC CTG AGA GAA CAG GCC GGC GGT GAC
Glu His Pro Gly Gly Glu Glu Val Leu Arg Glu Gln Ala Gly Gly Asp GCG ACT GAA AAC TTC GAA GAC GTT GGC CAT AGT ACC GAC GCT CGA GAA
Ala Thr Glu Asn Phe Glu Asp Val Gly His Ser Thr Asp Ala Arg Glu CTG TCG AAA ACG TAC ATC ATC GGT GAG CTG CAC CCG GAC GAT CGT TCT
Leu Ser Lys Thr Tyr Ile Ile Gly Glu Leu His Pro Asp Asp Arg Ser AAA ATC GCG AAA CCG TCC GAA ACT CTG TAA TGA GAATTCGATA TCAAGCTT
Lys Ile Ala Lys Pro Ser Glu Thr Leu End End

FIG. 6

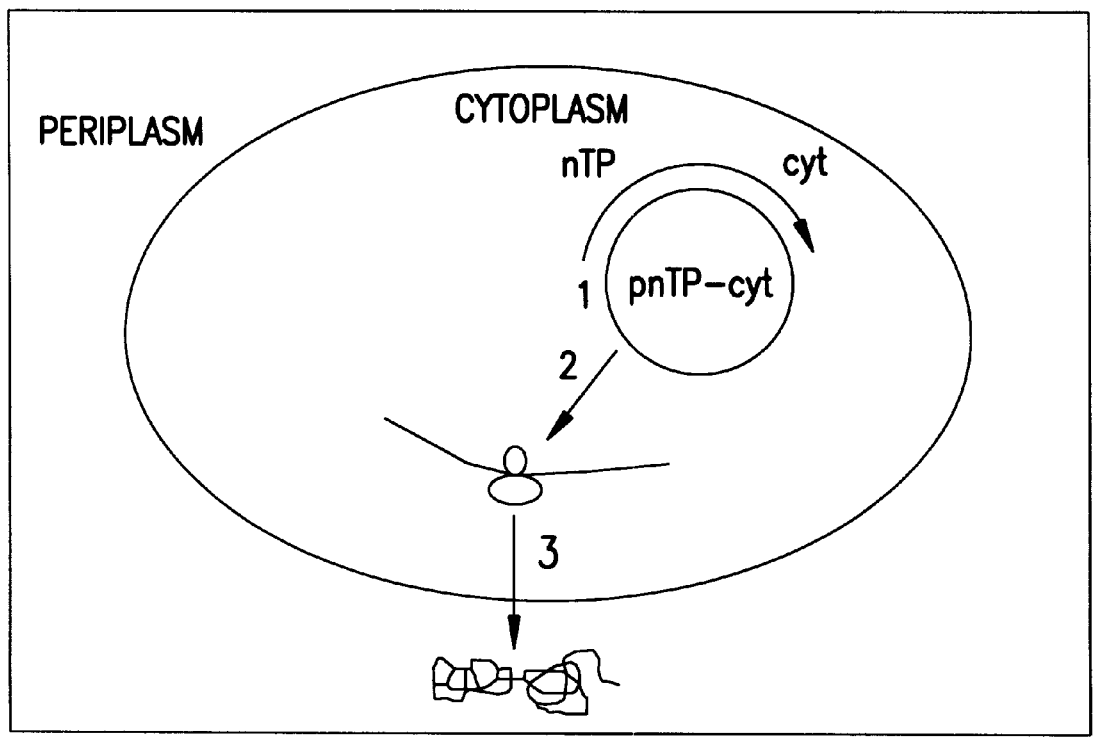
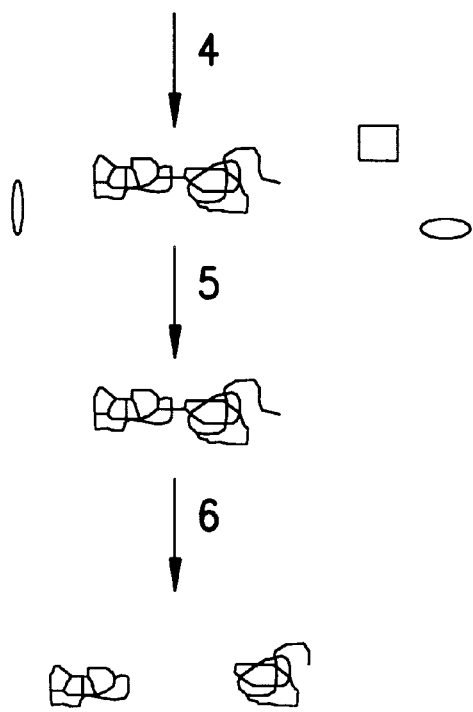
FIG. 9

PROTEIN FUSIONS FOR THE TRANSLOCATION OF APO-PROTEIN INTO THE PERIPLASMIC SPACE

FIELD OF THE INVENTION

The present invention is concerned with protein synthesis and in particular with the production of recombinant fusions between cytochrome $b_5$ and foreign proteins which can be translocated out of the cell into the periplasmic space of, for example, *Escherichia coli*.

BACKGROUND OF THE INVENTION

The mechanism by which a cytoplasmically-synthesised (recombinant) protein is translocated into the periplasmic space of *Escherichia coli* is known to occur by the workings of the signal hypothesis (see review by Stardler, J. A. and Silhavy, T. J., 1990, Methods in Enzymology, 167–187). Many such proteins are initially synthesised as precursor forms carrying extensions at their amino termini known as signal sequences (peptides). The signal sequence has the information required for selective translocation of the passenger part of the protein molecule across the cytoplasmic membranes of the bacteria. The signal is cleaved off soon after the periplasmically-deposited protein has gained its native biological fold and function.

SUMMARY OF THE INVENTION

Using this approach we have developed a bacterial system which allows production of chimeric or fusion forms of coloured proteins. These proteins are secreted into the periplasm where they are afforded greater protection against potential degradation.

According to a first aspect of the present invention there is provided a method of protein synthesis which comprises provision of a genetic unit comprising a nucleotide sequence coding for a pre-form of an apo-protein, synthesizing said pre-form apo-protein in a cytoplasmic region of a cell, and translocating said synthesised pre-form apo-protein to the periplasmic region of said cell, so as to permit constitution in said periplasmic region of a signal-processed apo-protein which can then be converted to the corresponding holo-protein.

According to a second aspect of the present invention, there is provided a genetic precursor unit which comprises a nucleotide sequence coding for a pre-form apo-protein, said nucleotide sequence being such that said pre-form apo-protein is translocatable from a cytoplasmic region of a cell to the periplasmic region of said cell, so as to permit constitution in said periplasmic region of a processed apo-protein and conversion into a corresponding holo-protein.

The genetic unit is preferably suitable for expression in the cytoplasmic region of a bacterial host cell, such as an *E.coli* host cell. The preferred *E.coli* strain is TB-1, [F ara Δ (lac-proAB) rps φ 80d lacZΔM15 hsdR17 (rk+$_m$+k)] or N4830-1 [f-suo his-ilv galK-(λ.ch1D-pg1)(λ.Bam N+CI857 H1)].

A preferred apo-protein comprises a cytoplasmic cytochrome, which typically comprises the soluble core domain of cytochrome $b_5$ of liver endoplasmic reticulum.

Cytochrome $b_5$ of the endoplasmic reticulum of mammalian liver is a well characterised, small haemoprotein of 16.7 kD which plays a central role in a variety of electron transfer reactions related to fatty acid desaturation, redox cycling of oestrogen and reduction of cytochrome P-450 reductase.

The hepatic cytochrome $b_5$ is composed of two domains, the above-described soluble, enzymatically active, haem-containing globular core ($b_5$) of about 12 kD and a smaller carboxy terminal tail anchored in the microsomal membrane. Within the tail portion, a stretch of 23 hydrophobic amino acid residues, also definable as an "insertion" sequence, autonomously and post-translationally integrates cytochrome $b_5$ into the lipid bilayer of the endoplasmic reticulum such that the active core domain is laterally disposed from the reticulum facing the cytoplasm.

It is preferred that the genetic unit further comprises a nucleotide sequence which codes for an amino-terminal signal peptide (the pre region of pre-form apo-protein) which is recognised by the cell to direct the pre-form apo-protein to the cytoplasmic membrane and thence subsequently translocated into the periplasm of the cell. The signal peptide typically comprises *E.coli* alkaline phosphatase, which is advantageously in linkage with cytochrome $b_5$ (apo-protein). The method therefore preferably further comprises the step of directing the apo-protein to the cytoplasmic membrane, under the direction of the signal peptide, so as to facilitate the above-described translocation of the pre-form apo-protein from the cytoplasm to the periplasmic space of the bacterium.

In this preferred embodiment of the present invention where the genetic unit further comprises a nucleotide sequence which codes for an amino-terminal signal peptide, the invention can be used to investigate signal peptidase which in vivo proteolytically cleaves N-terminal signal peptides.

Many proteins which are synthesised in the cytosol have to be targeted to various extracellular and subcellular locations. This involves translocation across one or more lipid bilayers impermeable to large hydrophilic molecules. A feature of most translocated proteins is that they are synthesised as precursor forms carrying N-terminal signal sequences, which as discussed above are proteolytically cleaved by signal peptidase, either during or immediately after transport of the passenger protein across the biological membrane.

Signal peptidase is highly specific as it cleaves only preprotein precursors. Although lacking sequence homologies, signal sequences are functionally highly conserved. Despite significant variations in their lengths, all signals have three definable regions, namely an N-terminal region carrying one or two basic residues, a middle core encompassing hydrophobic residues and a terminal region specifying the cleavage site.

The conventional assay for signal peptidase has until now relied on the use of natural precursor proteins which are synthesised in a cell-free translation system in a highly radioactive form. The extent of processing is monitored by incubating the radio-labelled substrate with either membranes or signal peptidase and monitoring the processed bands by autoradiography following gel electrophoresis. The assay is not only time-consuming and expensive but suffers from the use of minuscule quantities (fmol) of substrates in relation to enzyme quantities, with inevitable contamination by many cellular components derived from the use of in vitro synthesis systems.

We have now overcome the above problems, and there is further provided by the present invention an assay system for signal peptidase, which assay system comprises:

(a) a genetic precursor unit which comprises a nucleotide sequence coding for an apo-protein and an amino-terminal signal peptide, the nucleotide sequence being such that the apo-protein is translocatable from a cytoplasmic region of a cell to the periplasmic region of the cell, so as to permit constitution in said periplasmic region of a processed apo-protein; and (b) signal peptidase, a source thereof or a precursor therefor, wherein the signal peptidase can effect proteolytic cleavage of the amino terminal signal peptide from the apo-protein.

The genetic unit of the assay system is substantially as hereinbefore described and is advantageously suitable for expression in a bacterial medium such as E.coli and the assay system preferably further comprises a host medium such as E.coli substantially as hereinbefore described.

Preferably the assay system further comprises means for monitoring the proteolytic cleavage of the amino terminal signal peptide from the apo-protein. The monitoring means typically comprises means for separating the cleaved apo-protein from the pre-form apo-protein, and means for spectrophotometrically monitoring the cleaved apo-protein following supplementation thereof with exogenous haem. Typically the pre-form apo-protein is phase-separated from the cleaved apo-protein, the pre-form only being soluble as an aggregate in the presence of a detergent, the cleaved apo-protein being water soluble.

The provision of such an assay system is advantageous in investigating the mechanistic and structural properties of signal peptidase. A particularly useful application of an assay system according to the present invention is in the identification of inhibitors of signal peptidase which can subsequently be used as probes in investigating the reaction mechanism of signal peptidase.

There is further provided by the present invention a method of identifying inhibitors to signal peptidase, which method comprises providing an assay system substantially as described above, introducing a test material into cells of a host medium used in the assay system, and monitoring the effect of said test material on a selected activity of the signal peptidase.

Advantageously, the identification method involves monitoring the cleavage of the amino-terminal signal peptide from the apo-protein by spectrophotometric means substantially as hereinbefore described.

Preferably the test material comprises any of the following: a consensus signal peptide (which typically comprises a 19 residue peptide), one or more transition metal ions, and carboxy-modifying reagents.

Signal peptidase is a known crucial rate limiting step in the pathway of protein secretion and can offer a locus for control or regulation of an essential biofunction, namely protein export. Thus the identification of a signal peptidase inhibitor can provide a tool to understand the reaction mechanism of signal peptidase, and also, more importantly, a means to regulate growth of microorganisms and protein secretory disorders in higher organisms.

The invention allows the observation of the effects of competitive inhibition by selected inhibitors in order to identify the precise region of signal sequence that is essential for recognition/cleavage by signal peptidase.

There is further provided by the present invention a method of recognising an active binding site of signal peptidase, which method comprises contacting the signal peptidase with at least on photoactivatable form of a radiolabelled (typically radioiodinated) inhibitor of the peptidase, and identifying the binding location of the inhibitor to the peptidase.

There is further provided by the present invention, a test material identified as an inhibitor to signal peptidase, for use in modulating in vivo protein secretion.

The test material may advantageously comprise a synthetic inhibitor of signal peptidase, and has beneficial applications as a biocidal agent, regulating secretory disorders in mammalian cells, control of plant growth and the like.

The genetic unit typically comprises a plasmid having a vector as shown in any of FIGS. 1 to 3, or a DNA sequence as shown in any of FIGS. 4 to 6 (SEQ ID NOS 1 to 3, respectively). The most significant features of the plasmid sequences are as follows:

a) a native pho promoter for transcriptional control. The pho promoter is available coded for by the plasmids pSEC-cyt which is inducible by growth of the bacteria in a phosphate-limited medium;

b) a signal sequence coding for alkaline phosphatase as hereinbefore described; and c) a soluble cytochrome $b_5$ core gene sequence.

There is further provided by the present invention a genetic unit having a vector substantially as illustrated in any of FIGS. 1 to 3, or a DNA sequence as illustrated in any of FIGS. 4 to 6 (SEQ ID NOS 1 to 3 respectively), which is capable of generating translocated forms non-fusion (FIG. 1 or 4) or fusion (chimeric) forms of coloured cytochrome $b_5$ (FIGS. 2,5 and 3,6). The foreign protein can be tagged to the cytochrome $b_5$ protein at its carboxy (C) FIGS. 2,5) or amino (N) terminus (FIGS. 3,6).

The pho promoter is typically capable of minimising the lethality of the expressed chimera to the host by maintaining the expression of chimera under the tight transcriptional control of the native pho promoter, in plasmids pSEC-cyt/C and pSEC-cyt/N, inducible only by growth of the bacteria in a phosphate limited medium. In pSEC-cyt/C fusions are introduced by linkage of a foreign DNA sequence at the carboxy terminus of cytochrome $b_5$ gene through the unique BclI site. In pSEC-cyt/N fusions are introduced immediately at the N-terminus of cytochrome $b_5$ but after the signal sequence, through the unique BamHI and/or PstI sites.

The method of expression of the pre-form cytochrome $b_5$ or its chimeric derivative typically involves initiation of transcription, and hence protein synthesis, by control of the incubation conditions of the host medium. Typically the initiation stage comprises cultivation of the bacterial host in a phosphate-limited medium (0.1 mM phosphate), and spectrophotometric or visual monitoring (transformation of the colour of the bacterial cells from a grey to pink colour) of the synthesis cytochrome $b_5$ (processed) or its chimera (processed) in E.coli harbouring pAA-cyt or pSEC-cyt, respectively, under the transcriptional control of the pho promoter.

It is further preferred that the method involves translocation of a prosthetic group from the cytoplasmic region of the cell to the periplasmic region, for combination with the signal-processed apo-form of the chimeric protein in the periplasmic region to form the holo-protein as hereinbefore described. It is preferred that the apo-protein is first translocated to the periplasmic region, followed by subsequent translocation of the prosthetic group, such that the apo-protein can act as a sink for the latter. In the case where the apo-protein comprises the cytochrome $b_5$ soluble core, the prosthetic material comprises the haem (protoporphyrin IX) prosthetic group. The periplasmic accrual of the apo cytochrome $b_5$ core is thought to trigger the subsequent translocation of the haem-prosthetic group.

It is envisaged that a prosthetic material may be present in the periplasmic region of the cell, although this does not appear to be the case with cytochrome $b_5$ due to the observed build up of periplasmic apo-cytochrome $b_5$ and ensuing time lag preceding the appearance of periplasmic holo-cytochrome $b_5$.

Production of the exported periplasmically-localised haemoprotein can typically exceed 6 mg/liter of culture after five hours induction. Mutated forms of the cytochrome $b_5$ have been developed which can enhance exportation of the mature forms by more than tenfold. The approach may be useful for the production and secretion of coloured forms and fusions in eukaryotic cells.

The method according to the invention typically further comprises monitoring of protein synthesis by observing the visual transformation of the bacterial cells from a grey translucent to a bright pink colour. This colour change is due to the expression of the cytochrome $b_5$ gene. The monitoring may be carried out by spectrophotometric means where an accurate analysis of the extent of protein synthesis is required, so allowing the protein synthesis to be terminated when sufficient protein has been synthesised.

The above-described method allows a prokaryotic signal sequence to be appended with cytochrome $b_5$, such that this natural cytoplasmic protein of eukaryotic origin is transformed into a secretory form in *E.coli*. Furthermore, the expression of the eukaryotic gene encoding the pre-form apo-protein or its chimera, synthesised in the cytoplasm, is such that the post-translocationally processed component in the periplasm gives rise to the holo-protein or its fusion counterpart.

According to the present invention there is further provided a proteinaceous material comprising a pre-form apo-protein which is synthesised in the cytoplasmic region of a cell, the pre-form apo-protein being translocatable to the periplasmic region of said cell, so as to allow constitution in said periplasmic region of a correspondingly processed apo-protein, the binding of a prosthetic group (typically the haem group) to the apo-protein forms the holo-protein.

There is further provided by the present invention an apo-protein substantially as hereinbefore described, in combination with a signal peptide for selective translocation (export) or secretion of said apo-protein from the cytoplasmic to the periplasmic region of a cell, so as to allow constitution in the periplasmic region of a corresponding holo-protein from said apo-protein.

According to yet a further aspect of the present invention there is provided a holo-protein constituted in the periplasmic region of a cell from an apo-protein, or by a method, substantially as hereinbefore described. There is further provided a holo-protein derived from a genetic precursor unit, substantially as illustrated with reference to any of FIGS. 4 to 6.

The above-described apo- and holo-proteins typically respectively comprise the apo- and holo- forms of cytochrome $b_5$ or its respective N- or C-terminally fused chimeric forms. The fusions can be generated at either the amino or carboxy terminus of the secreted recombinant protein.

There is further provided by the present invention an *E.coli* host medium containing a genetic precursor unit substantially as hereinbefore described.

There is further provided a kit for use in protein synthesis, which kit comprises:
a) a bacterial host medium substantially as hereinbefore described; and
b) genetic material comprising a nucleotide sequence coding for a pre-form apo-protein, such that said pre-form apo-protein coded for by said nucleotide sequence is translocatable from the cytoplasmic to the periplasmic region of a cell of the host medium, so as to allow constitution in the periplasmic region of a holo-protein from the apo-protein.

The kit typically comprises a bacterial host medium, such as *E.coli,* together with genetic material comprising precursor constituent genes suitable to be included in a genetic unit substantially as hereinbefore described.

An example of a typical synthesis of a fusion protein according to the present invention will now be described.

A gene coding for a foreign protein or peptide was fused in a reading frame from either (i) the carboxy-terminus or (ii) the N-terminus of the soluble core of cytochrome $b_5$. The foreign gene was ligated between either (i) the unique BclI restriction site and the downstream polylinker site or (ii) the unique PstI and BamHI site located between the signal sequence and cytochrome $b_5$.

*E.coli* TB-1 (Lac) cells were then transformed with the ligation mixture.

Transformants were plated out on Luria broth agar (1.5% (w.v)) plates containing ampicillin (75 μg/ml), isopropyl-β-D-galactopyranoside (IPTG) (100 μM),5-bromo-4-chloro-3-indolyl-β-D-galactoside (X-gal) (20 μg/ml). Transformant colonies bearing potential inserts were white in colour whereas non-recombinants were blue in colour. If required, the recombinant plasmids could be further verified by restriction mapping.

For induction, a starter bacterial culture cultivated to saturation in LB/ampicillin was applied at a 2% (v/v) inoculum into MOPS medium. The cultures were grown with shaking at 100 revs/min at 35° C. for 5 to 10 h.

The following table indicates the composition of the MOPS medium. All solutions were sterilised by autoclaving or filter sterilisation. The final concentration of phosphate in the MOPS medium was about 0.1 mM.

| Component | % (v/v) in MOPS |
|---|---|
| Water | 74.5 |
| M$^a$ | 20 |
| O$^f$ | 0.2 |
| P$^a$ | 0.01 |
| S$^a$ | 0.1 |
| VFCAA$^a$ | 2 |
| 20% glucose$^f$ | 1 |
| 0.05% thiamine B1$^f$ | 0.2 |
| 25 mg/ml ampicillin$^f$ | 0.3 |

M, 4.2% (w/v) MOPS buffer, 0.4% (w/v) Tricine, 1.46% NaCl, 0.8% KOH, 0.2555% NH$_4$Cl
O, 5.36% MgCl$_2$, 0.16% HCl, 0.1% FeCl$_2$, 0.00368% CaCl$_2$.2H$_2$O, 0.00128% H$_3$BO$_3$, 0.0008% MnCl$_2$.4H$_2$O, 0.00036% CoCl$_2$.H$_2$O, 0.00008% CuCl$_2$.2H$_2$O, 0.0068% ZnCl$_2$, 0.0121% Na$_2$MoO$_4$.2H$_2$O.
P, 1.0M KH$_2$PO$_4$
S, 0.276M K$_2$SO$_4$
VFCAA, 7.5% vitamin-free Casamino acids
$^a$autoclaved prior to use
$^f$filter sterilised prior to use Positive expression of the fusion protein was indicated by pink colour of the bacterial cells obtained by centrifugation at 5,000×g for 5 min.

The protein was extracted from the bacteria by the following "osmotic shock" method:
(i) The cells (derived from a 30 ml culture) were gently suspended in 1 ml of 20% sucrose, 0.3 M Tris-HCl (pH 8), 1 mM Na$_2$EDTA)(STE) and incubated at room temperature (22° C.) for 10 min.
(ii) The cells were then harvested as pellet by centrifugation at 5,000×g for 6 min and thoroughly resuspended in residual STE volume.
(iii) The plasmolysed cells were osmotically shocked by rapidly suspending in ice-cold 0.5 mM MgCl$_2$ and left on ice for 10 min.

Centrifugation at 10,000×g for 10 min yielded supernatant comprising the periplasmic fraction. Pink coloration of the supernatant implied that fusion protein had been efficiently extracted from the periplasmic space.

The quantity of the recombinant protein was monitored by subjecting a fraction of the extract to a spectral scan from 350 to 500 nm. The oxidised cytochrome was identifiable by the rise in absorbance at 413 nm. Often a significant pool of the apo-protein may be present. This may be converted to holo cytochrome by addition of haem to the supernatant to a final concentration ranging from 5 to 20 μM; an equivalent amount of haem was added to the blank cuvette to counteract the absorbance rise by excess haem in the sample. The amount of protein may be calculated from the mM extinction coefficient of the oxidised cytochrome $b_5$ of 115 and 413 nm.

BRIEF DESCRIPTION OF THE DRAWINGS

The present invention will now be further illustrated, by way of example only, by reference to the accompanying FIGS. 1 to 6, wherein:

FIGS. 4–6 illustrate the genetic sequences of the vectors respectively illustrated in FIGS. 1–3 (SEQ ID NOS 1 to 3, respectively); and FIGS. 7–9 schematically illustrate modifications of plasmids according to the present invention, which involve cloning, expression and isolation of the chimeric proteinaceous material.

DETAILED DESCRIPTION OF THE INVENTION

Figure 1:
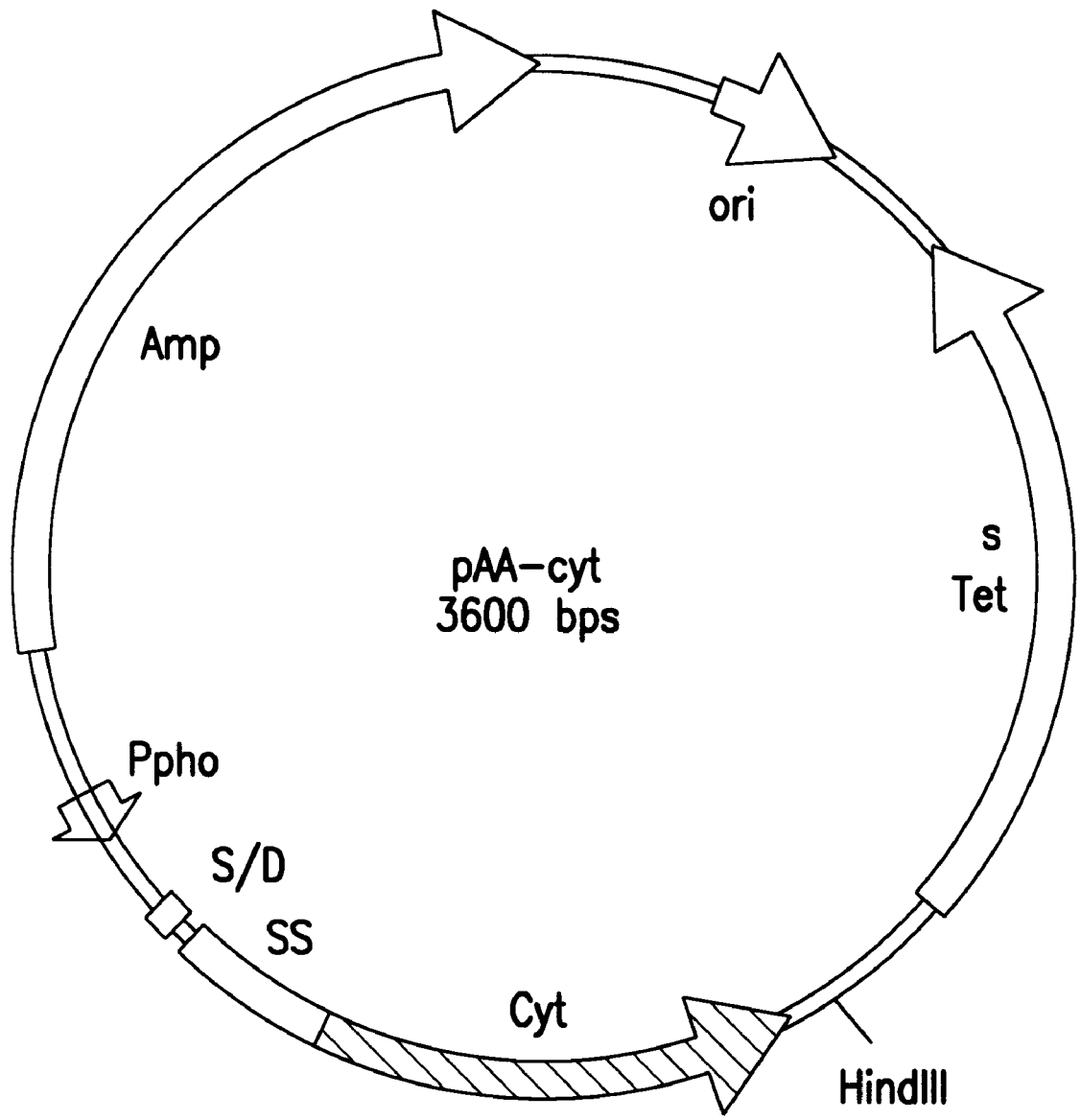
FIGS. 1,2 and 3 illustrate expression vectors pAA-cyt, pSEC-cyt/C and PSEC-cyt/N of a genetic unit according to the present invention.

FIG. 1 illustrates plasmid PAA-cyt constructed for the periplasmic production of non-fusion, secreted holo-cytochrome $b_5$.

Figure 2:
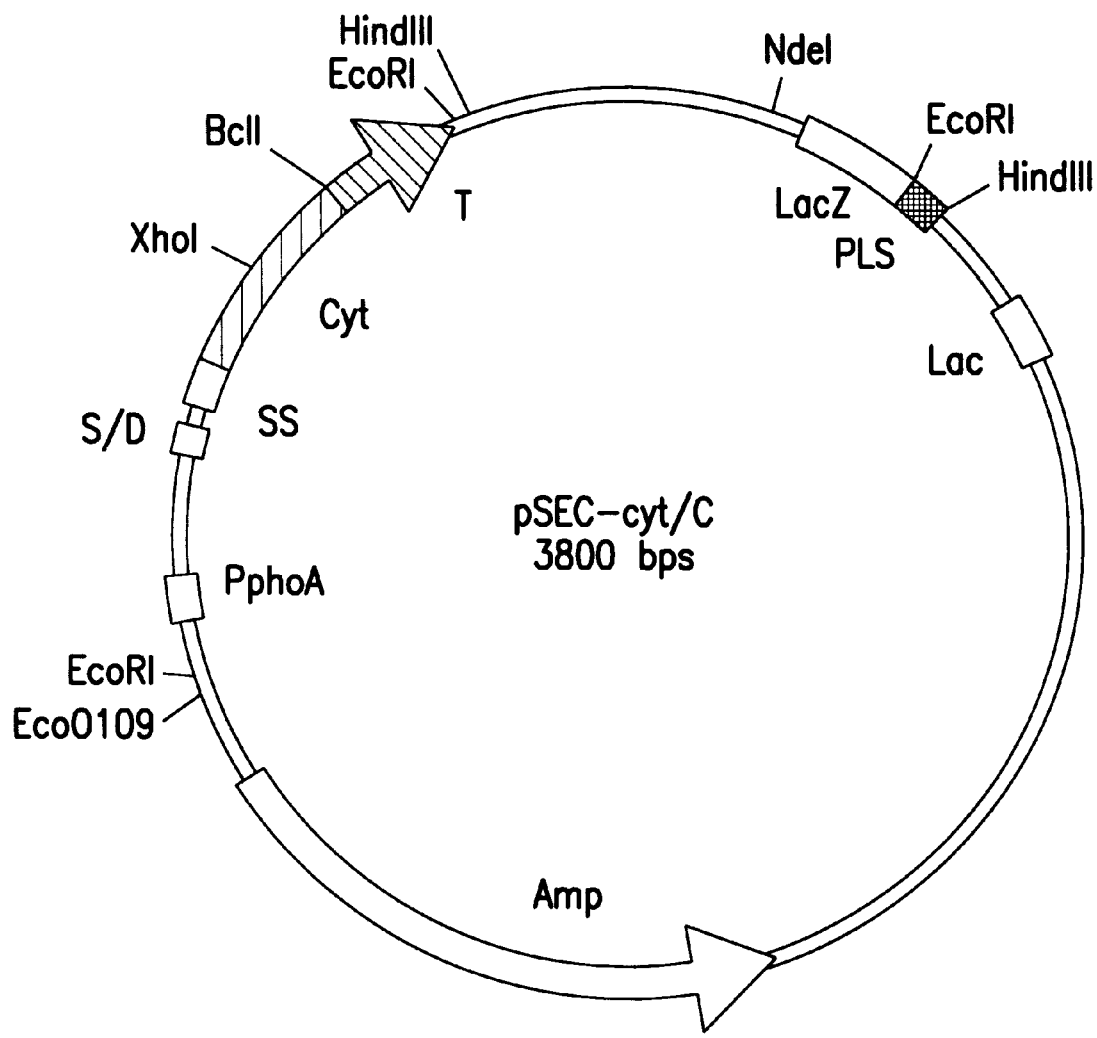

FIG. 2 illustrates the plasmid PSEC-cyt/C constructed for linkage at the 3' terminus (C-terminus) of the soluble cytochrome $b_5$ core gene with a foreign gene sequence, according to the present invention.

Figure 3:
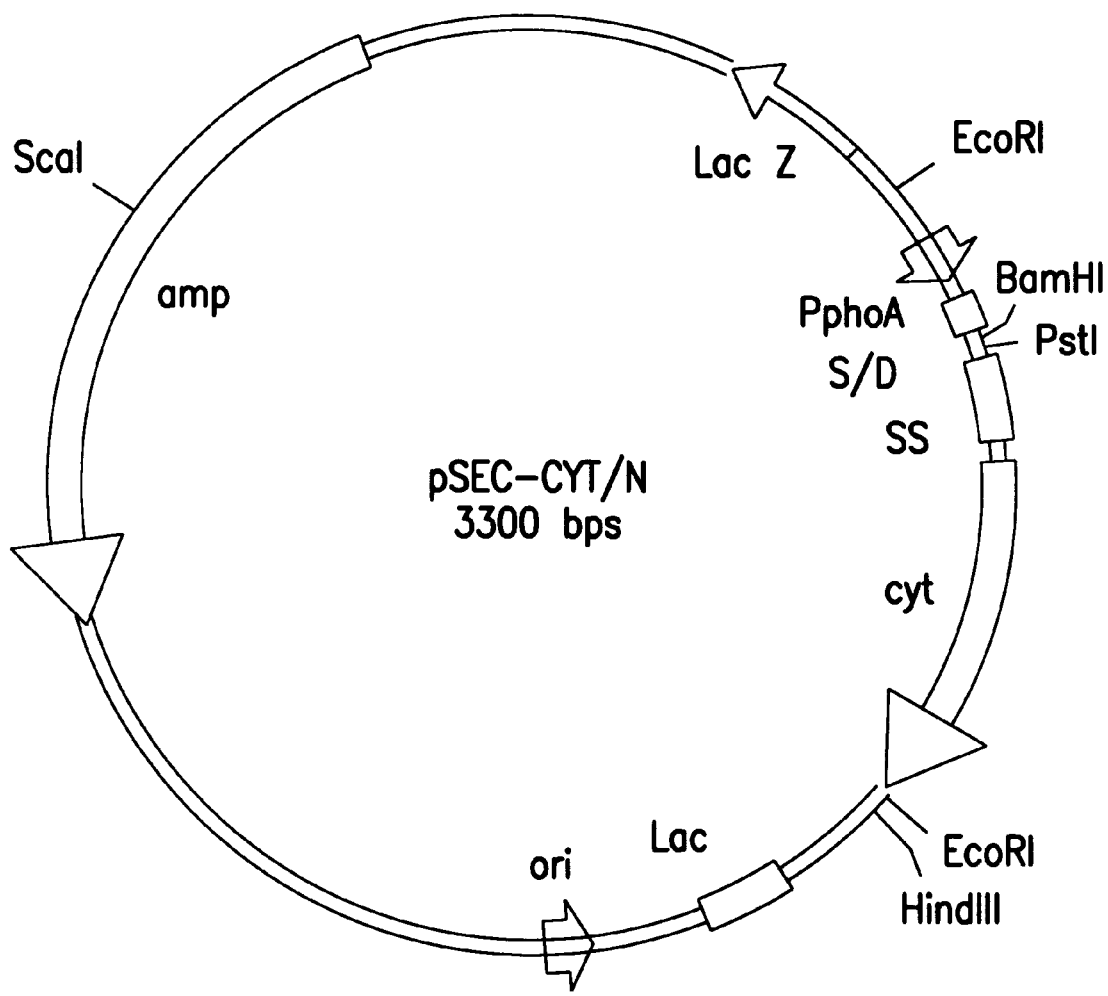

FIG. 3 illustrates the plasmid PSEC-cyt/N for linkage at 5' terminus, between the C-terminus of alkaline phosphatase signal and the N-terminus of cytochrome $b_5$ of the cytochrome $b_5$ core gene, according to the present invention.

Referring now to FIGS. 1 to 3, the essential features of the illustrated vector are as follows:

Pho, Pho promoter activated in bacteria grown on phosphate limited medium;

S/D), Shine Dalgarno sequence for translation initiation of alkaline phosphatase signal;

SS, alkaline phosphatase signal sequence gene encoding 21 residue signal including the first arginine residue of mature alkaline phosphatase;

Cyt, soluble core of cytochrome $b_5$;

T, tail of the native cytochrome $b_5$;

Lac, Lactose operon promoter; and

PLS, polylinker sites: EcoRI, (Hind III), SacI, KpnI, SmaI, BamHI, XbaI, SalI, HincII, BspMI, PstI, SphI, HindIII. (In the polylinker sites, EcoRI and HindIII can be in the reverse order to that shown.)

SS-cyt/C, codes for the complete precursor of the cytochrome $b_5$ including the tail portion of the haemoprotein.

Figure 7A:
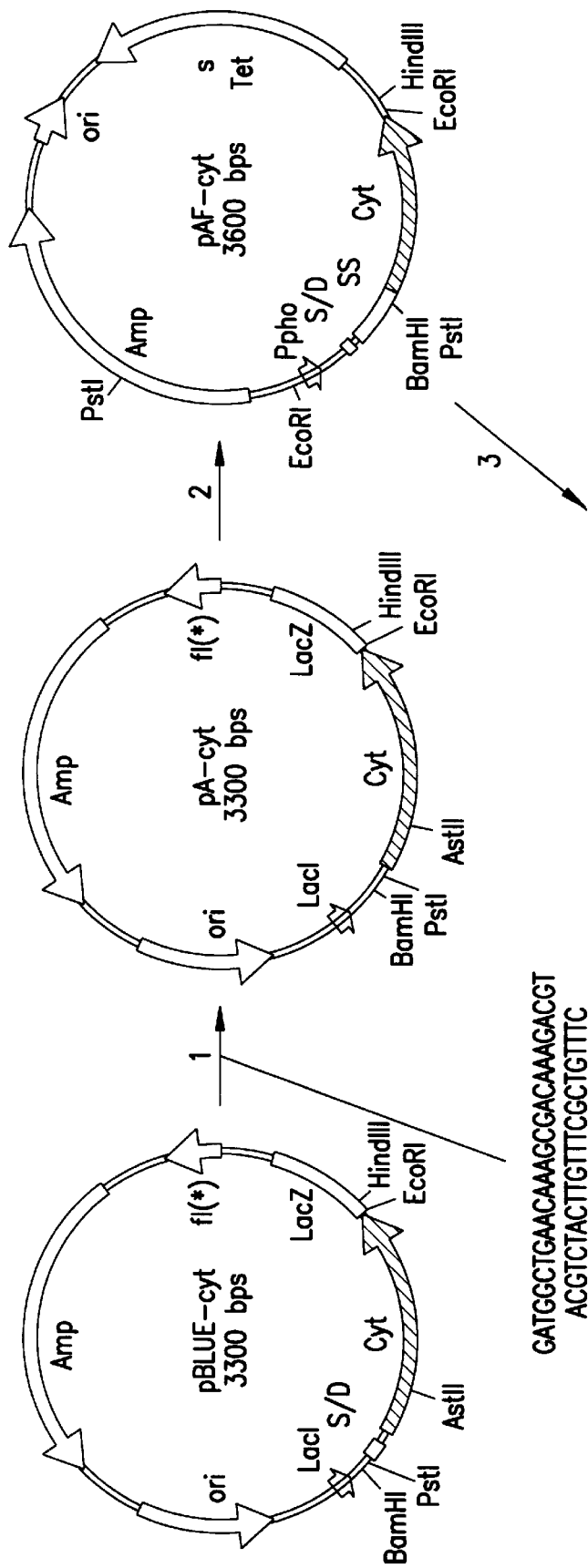
Figure 7B:
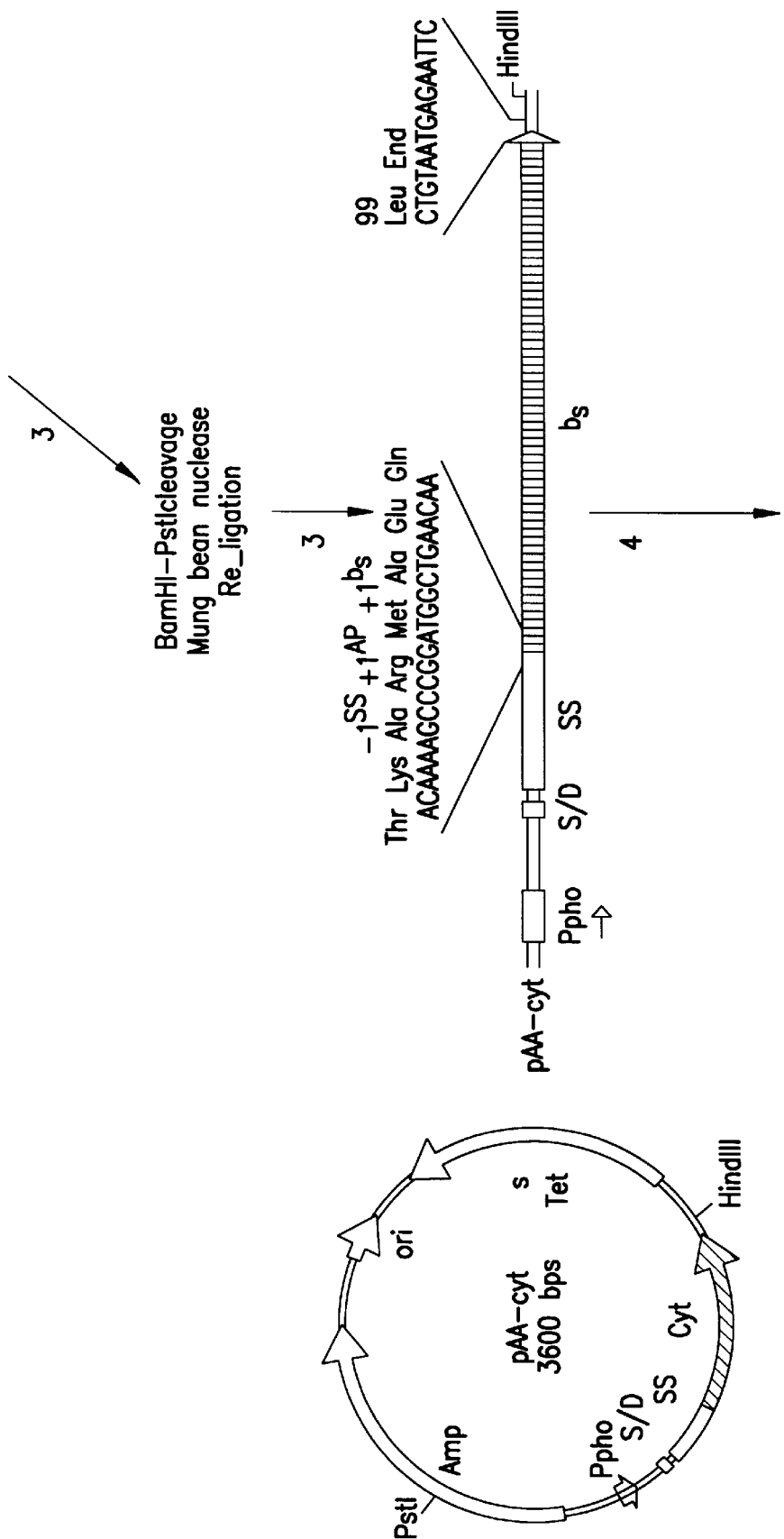
Figure 7C:
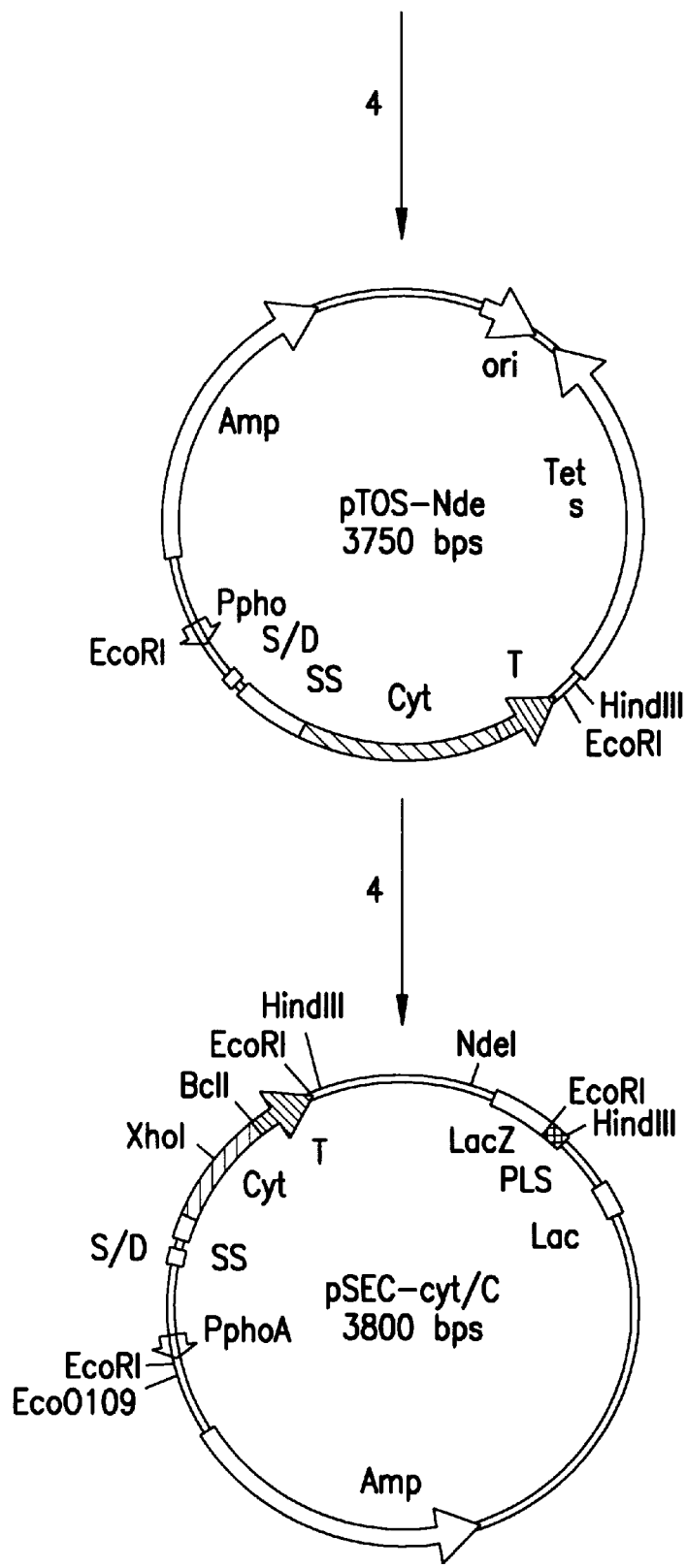

Referring now to FIG. 7, the figure illustrates the scheme of appendage of alkaline phosphatase signal to rat liver ER cytochrome $b_5$ in plasmid constructions pAA-cyt, pSEC-cyt/C and pSEC-cyt/N. The full-length synthetic cytochrome $b_5$ gene, contained within the PstI-EcoRI sites and carrying an in-built ribosomal binding site, was cloned within the polylinker site of pBluescript SK+ to give pBLUE-cyt. In step 1, the unique PstI site, located upstream of the Shine/Dalgarno sequence of cytochrome $b_5$ gene was displaced immediately adjacent to the cytochrome $b_5$ methionine initiator codon by replacing PstI-AatII deletion with the 27 bp synthetic oligonucleotide duplex. This gave plasmid pA-cyt. Icyt. In step 2, insertion of the modified BamHI-HindIII-cleaved cytochrome $b_5$ gene (from pA-cyt) into identically-cleaved pFOG402. This yielded plasmid pAF-cyt in which cytochrome $b_5$ is placed under the control of phoA promoter but in an unphased reading frame with the alkaline phosphatase signal sequence. In step 3, involving construction of pAA-cyt, it shows the generation of the correct reading frame between the signal sequence and cytochrome $b_5$ by flush-ending PstI-BamHI- cleaved PAF-cyt and recircularising the plasmid. In this process the 21 residue signal sequence was installed in a contiguous reading frame with the mammalian cytochrome $b_5$ such that the +1 arginyl residue of mature alkaline phosphatase became included. This was to enhance the export properties of the cytochrome $b_5$ apo-protein. To minimise lethality to the host, the chimera was placed under tight transcriptional control of the native pho promoter in plasmid pAA-cyt, inducible by growth of the bacteria in a phosphate-limited medium. In step 4, the plasmid was further modified by appending the tail portion (T) of cytochrome $b_5$. Finally, translocation of EcoO109-cleaved cytochrome $b_5$-T segment into identically cleaved PUC19 gave plasmid PSEC-cyt/C.

Plasmid PSEC-cyt/N was derived by excising EcoRI-HindIII fragment from PAF-cyt containing pho-A-ss-$b_5$ and cloning into identically cleaved pUC19.

Figure 8:
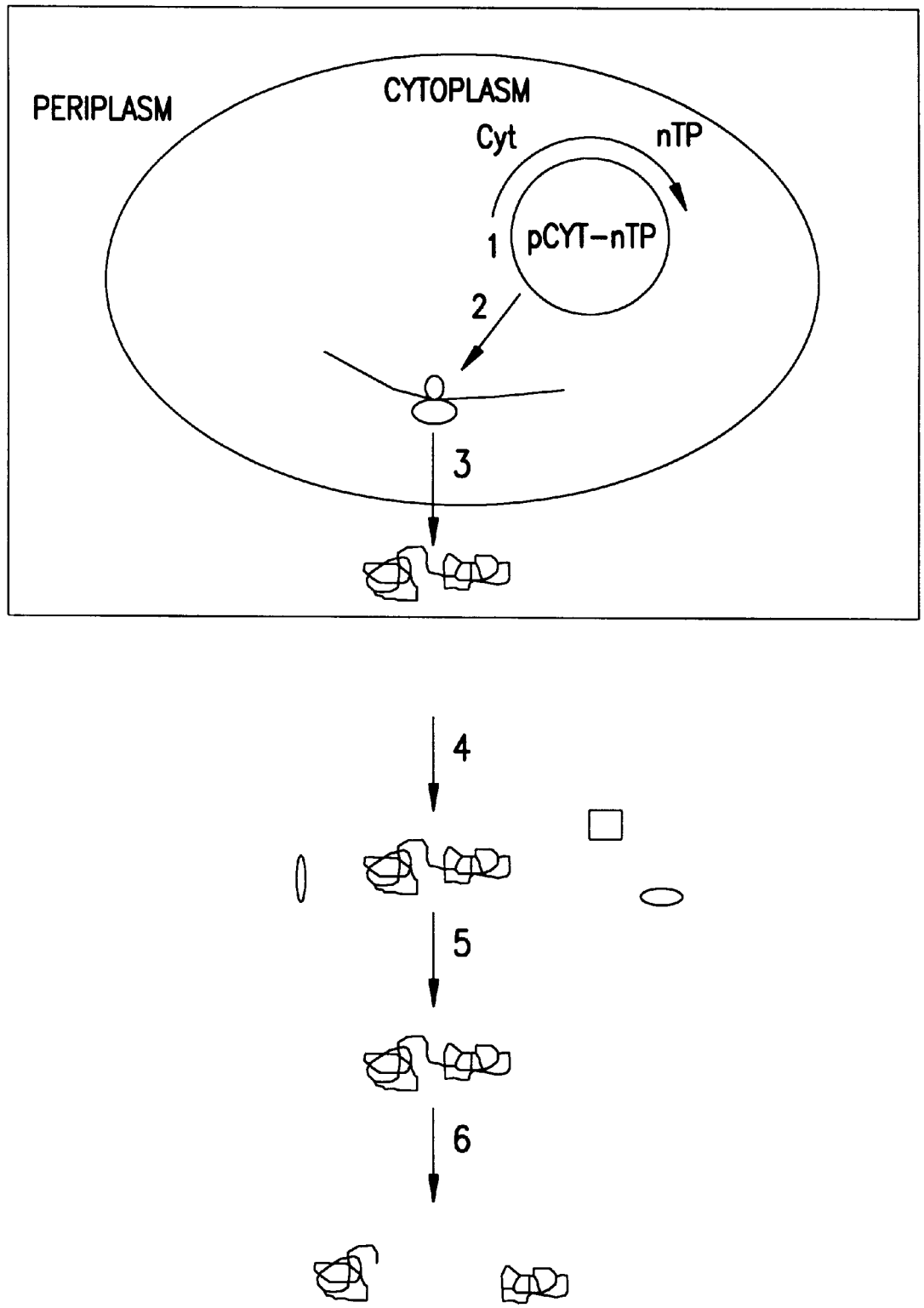

Referring now to FIG. 8, an expression vector as illustrated in FIG. 2 was modified by appending in fusion at the C-terminus of cytochrome $b_5$ with a gene sequence coding for the transit peptide of nitrite reductase (step 1). The modified plasmid (pCYT-nTP) was introduced into the cytoplasmic region of E.coli TB-1 (Lac) cells and the corresponding chimeric protein comprising the cytochrome $b_5$ apo-protein fused at its C-terminus with nitrite reductase transit peptide (pre-form apo-form of cytochrome $b_5$-nitrite reductase transit peptide), was expressed in the cytoplasm (step 2). The pre-form chimeric protein was processed (apo form of cytochrome $b_5$-nitrite reductase transit peptide) and after being translocated into the periplasmic region of the E.coli cells (step 3), it combined with the haem-prosthetic group to give the holo-protein (holo form of cytochrome $b_5$-nitrite reductase transit peptide).

The crude recombinant chimeric protein was extracted from the pink bacteria (20 ml culture) by an osmotic shock technique (step 4). The technique involved suspending the cells in 1 ml of 20% sucrose, 0.3M Tris-HCl (pH 8), 1 mM $Na_2$EDTA (STE) and incubation at room temperature for ten minutes. The cells were harvested as pellet by centrifugation at 5,000 g for six minutes and resuspended in residual STE volume. The plasmolysed cells were osmotically shocked by suspending in a minimum possible volume (approximately 5 ml) of ice-cold 0.5 mM $MgCl_2$ and left on ice for 10 minutes, followed by centrifugation at 10,000 g for ten minutes to yield a supernatant comprising the periplasmic fraction of the cells.

The chimera traced by its bright pink colour was purified by a single-step affinity chromatography (step 5), such as DEAE Sepharose column chromatography or haem-affinity chromatography. The chimera was then selectively cleaved (step 6) by CNBr treatment to generate authentic nitrite reductase transit peptide.

The 21 residue signal sequence is installed in a contiguous reading frame with the mammalian cytochrome $b_5$, the +1 arginyl residue of mature alkaline phosphatase being included to enhance the export properties of the apo-protein chimera.

Referring now to FIG. 9, an expression vector as illustrated in FIG. 3 was modified by inserting in a contiguous reading between the signal sequence and cytochrome $b_5$, a BamHI-PstI synthetic gene coding for nitrite reductase transit peptide (step 1). The derivative plasmid (pnTP-cyt) was introduced into the cytoplasmic region of *E.coli* TB-1 (Lac) cells and the corresponding chimeric protein comprising the pre-form apo-form of nitrite reductase transit peptide-cytochrome $b_5$ was expressed in the cytoplasm (step 2). The processed form of the chimeric protein (apo-form of nitrite reductase transit peptide-cytochrome $b_5$) was then translocated into the periplasmic region of the *E.coli* cells (step 3), where combination with the haem-prosthetic group occurred constituting the holo-protein.

The crude recombinant protein was extracted from the pink bacterial (20 ml culture) by an osmotic shock technique (step 4). The technique involved suspending the cells in 1 ml of 20% sucrose, 0.3M Tris-HCl (pH 8), 1 mM $Na_2EDTA$ (STE) and incubation at room temperature for ten minutes. The cells were harvested as pellet by centrifugation at 5,000 g for 6 minutes and resuspended in residual STE volume. The plasmolysed cells were osmotically shocked by suspending in a minimum possible volume (approximately 5 ml) of ice-cold 0.5 mM $MgCl_2$ and left on ice for 10 minutes, followed by centrifugation at 10,000 g for ten minutes to yield a supernatant comprising the periplasmic fraction of the cells.

The chimera traced by its bright pink colour was purified by a single-step affinity chromatography (step 5), such as DEAE Sepharose column chromatography or haem-affinity chromatography. The nitrite reductase transit peptide was cleaved from the isolated chimera by CNBr.

The 21 residue signal sequence is installed in a contiguous reading frame with the foreign gene and the subsequent mammalian cytochrome $b_5$. The +1 arginyl residue of mature alkaline phosphatase being included to enhance the export and processing characteristics of the chimeric apo-protein.

I claim:

1. A genetic precursor unit which comprises
   (a) a nucleotide sequence coding for a pre-form cytoplasmic cytochrome apo-protein
   (b) a nucleotide sequence coding for an amino-terminal signal peptide operationally linked to said nucleotide sequence coding for a pre-form cytoplasmic cytochrome apo-protein, said signal peptide capable of directing said pre-form cytoplasmic cytochrome apo-protein to the cytoplasmic membrane of a cell for translocation into the periplasm of said cell; and
   (c) a pho promoter operationally linked to the nucleotide sequences coding for said pre-form cytoplasmic cytochrome apo-protein and said signal peptide.

2. A genetic unit according to claim 1, which is suitable for expression in the cytoplasmic region of an E.coli cell.

3. A genetic unit according to claim 2, wherein said E.coli cell comprises E.coli strain TB-1, [F ara$\Delta$(lac-proAB) rps$\phi$80d lacZ$\Delta$M15 hsdR17 (rk+$_m$$^+$k)] or N4830-1 [f-suo his-ilv-galK-($\lambda$ch1D-pg1)($\lambda$Bam N+CI857 H1)].

4. A genetic unit according to claim 1, wherein said cytoplasmic cytochrome comprises the soluble core domain of cytochrome $b_5$ of liver endoplasmic reticulum.

5. A genetic unit according to claim 1, wherein said signal peptide comprises E.coli alkaline phosphatase.

6. A method of protein synthesis which comprises the genetic precursor unit set forth in claim 1, synthesizing said pre-form cytoplasmic cytochrome apo-protein in a cytoplasmic region of a cell, and translocating said synthesized pre-form cytoplasmic cytochrome apo-protein to the periplasmic region of said cell, so as to permit constitution in said periplasmic region of a signal-processed cytoplasmic cytochrome apo-protein which can then be converted to a corresponding holo-protein.

7. A method according to claim 6, wherein said cell comprises an E.coli cell.

8. A method according to claim 7, wherein said E.coli comprises E.coli strain TB-1, [F ara $\Delta$(lac-proAB)rps$\phi$80d lacZ$\Delta$M15 hsdR17 (rk+$_m$$^+$k)] or N4830-1 [f-suo his-ilv-galK-($\lambda$ch1D-pg1)($\lambda$Bam N+CI857 H1)].

9. A method according to claim 6, which comprises initiation of transcription of said genetic precursor unit by cultivating a bacterial host in a phosphate-limited medium.

10. A method according to claim 6, which comprises spectrophotometric or visual monitoring of a characteristic color change of host bacterial cells which is indicative of the synthesis of said holo-protein or its fusion counterpart in said bacterial cells.

11. A method according to claim 6, which comprises translocation of a prosthetic group from the cytoplasmic region of the cell to the periplasmic region, for combination with the signal-processed apo-protein in the periplasmic region to form the holo-protein.

12. A method according to claim 11, wherein the apo-protein is translocated to the periplasmic region, followed by translocation of the prosthetic group, such that the apo-protein can act as a sink for the latter.

13. A method according to claim 11, wherein the apo-protein comprises the cytochrome $b_5$ soluble core, and the prosthetic material comprises the haem prosthetic group.

14. A method according to claim 6, wherein synthesis of the holo-protein is at a level of at least 6 mg/liter of culture after five hours induction.

15. Apparatus for use in protein synthesis, which apparatus comprises:
    (a) a source of a bacterial cellular medium; and
    (b) a source of genetic material comprising a genetic precursor unit of claim 1.

16. Apparatus according to claim 15, wherein said bacterial medium comprises E.coli.

17. An assay system for a signal peptidase, said assay system comprising:
    (a) the genetic precursor unit of claim 1; and
    (b) a signal peptidase, a source thereof or a precursor therefor.

18. An assay system according to claim 17, wherein said genetic unit is suitable for expression in the cytoplasmic region of an E.coli cell.

19. An assay system according to claim 17, which further comprises a host medium for said genetic unit.

20. An assay system according to claim 19, wherein said host medium comprises E.coli.

21. An assay system according to claim 20, wherein said E.coli comprises E.coli strain TB-1, [F ara$\Delta$(lac-proAB) rps $\phi$80d lacZ$\Delta$M15 hsdR17 (rk+$_m$$^+$k)] or N4830-1 [f-suo his-ilv-galK-($\lambda$ch1D-pg1)($\lambda$Bam N+CI857 H1)].

22. An assay system according to claim 17, wherein said cytoplasmic cytochrome comprises the soluble core domain of cytochrome $b_5$ of liver endoplasmic reticulum.

23. An assay system according to claim 17, wherein said signal peptide comprises E.coli alkaline phosphatase.

24. An assay system according to claim 17, which further comprises means for monitoring the proteolytic cleavage of the amino terminal signal peptide from the apo-protein.

25. An assay system according to claim 24, wherein said monitoring means comprises means for separating the cleaved apo-protein, and means for spectrophotometrically monitoring the cleaved apo-protein following supplementation thereof with exogenous haem.

26. An assay system according to claim 25, wherein the pre-form apo-protein is phase-separated from the cleaved apo-protein.

27. A method of identifying inhibitors to signal peptidase, which method comprises providing an assay system according to claim 17, introducing a test material into cells of a host medium used in said assay system, and monitoring the effect of said test material on a selected activity of said signal peptidase.

28. A method according to claim 27, which involves spectrophotometrically monitoring the cleavage of amino-terminal signal peptide from the apo-protein.

29. A method according to claim 27, wherein the test material comprises any of consensus signal peptide, at least one transition metal ion and a carboxy-modifying reagent.

30. A vector as illustrated in any of FIGS. 1 to 3.

31. A DNA sequence as illustrated in any of FIGS. 4 to 6 (SEQ ID NOS 1 to 3 respectively).

* * * * *

UNITED STATES PATENT AND TRADEMARK OFFICE
CERTIFICATE OF CORRECTION

PATENT NO.: 5,962,222

DATED: October 5, 1999

INVENTOR(S): Mustak Ali Kaderbhai et al.

It is certified that error appears in the above-identified patent and that said Letters Patent is hereby corrected as shown below:

On the title page, item [73]:
    Insert --Assignee: University College of Wales, Aberystwyth, Dyfed, United Kingdom--.

Signed and Sealed this

Sixth Day of March, 2001

*Attest:*

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 495 base pairs
      (B) TYPE: nucleic acid
      (C) STRANDEDNESS: single
      (D) TOPOLOGY: circular (ii) MOLECULE TYPE: DNA (genomic)

(vi) ORIGINAL SOURCE:
      (A) ORGANISM: Escherichia coli
      (B) STRAIN: TB-1

(xi) SEQUENCE DESCRIPTION: SEQ ID NO: 1:

```
GTCAGTAAAA AGTTAATCTT TTCAACAGCT GTCATAAAGT TGTCACGGCC GAGACTTATA      60

GTCGCTTTGT TTTTATTTTT TAATGTATTT GTACATGGAG AAAATAAAGT GAAACAAAGC     120

ACTATTGCAC TGGCACTCTT ACCGTTACTG TTTACCCCTG TGACAAAAGC CCGGATGGCT     180

GAACAAAGCG ACAAAGACGT CAAATACTAC ACTCTGGAAG AAATCCAAAA ACACAAAGAC     240

TCGAAGTCGA CGTGGGTGAT CCTGCACCAT AAAGTATACG ACCTAACTAA ATTCCTCGAA     300

GAGCACCCCG GGGGCGAAGA AGTCCTGAGA GAACAGGCCG GCGGTGACGC GACTGAAAAC     360

TTCGAAGACG TTGGCCATAG TACCGACGCT CGAGAACTGT CGAAAACGTA CATCATCGGT     420

GAGCTGCACC CGGACGATCG TTCTAAAATC GCGAAACCGT CCGAAACTCT GTAATGAGAA     480

TTCGATATCA AGCTT                                                     495
```

(2) INFORMATION FOR SEQ ID NO: 2:

(i) SEQUENCE CHARACTERISTICS:
      (A) LENGTH: 3918 base pairs
      (B) TYPE: nucleic acid
      (C) STRANDEDNESS: single
      (D) TOPOLOGY: circular (ii) MOLECULE TYPE: DNA (genomic)

(xi) SEQUENCE DESCRIPTION: SEQ ID NO: 2:

```
TCGCGCGTTT CGGTGATGAC GGTGAAAACC TCTGACACAT GCAGCTCCCG GAGACGGTCA     60
CAGCTTGTCT GTAAGCGGAT GCCGGGAGCA GACAAGCCCG TCAGGGCGCG TCAGCGGGTG    120
TTGGCGGGTG TCGGGGCTGG CTTAACTATG CGGCATCAGA GCAGATTGTA CTGAGAGTGC    180
ACCATATGCG GTGTGAAATA CCGCACAGAT GCGTAAGGAG AAAATACCGC ATCAGGCGCC    240
ATTCGCCATT CAGGCTGCGC AACTGTTGGG AAGGGCGATC GGTGCGGGCC TCTTCGCTAT    300
TACGCCAGCT GGCGAAAGGG GGATGTGCTG CAAGGCGATT AAGTTGGGTA ACGCCAGGGT    360
TTTCCCAGTC ACGACGTTGT AAAACGACGG CCAGTGAATT CGAGCTCGGT ACCCGGGGAT    420
CCTCTAGAGT CGACCTGCAG GCATGCAAGC TTGGCGTAAT CATGGTCATA GCTGTTTCCT    480
GTGTGAAATT GTTATCCGCT CACAATTCCA CACAACATAC GAGCCGGAAG CATAAAGTGT    540
AAAGCCTGGG GTGCCTAATG AGTGAGCTAA CTCACATTAA TTGCGTTGCG CTCACTGCCC    600
GCTTTCCAGT CGGGAAACCT GTCGTGCCAG CTGCATTAAT GAATCGGCCA ACGCGCGGGG    660
AGAGGCGGTT TGCGTATTGG GCGCTCTTCC GCTTCCTCGC TCACTGACTC GCTGCGCTCG    720
GTCGTTCGGC TGCGGCGAGC GGTATCAGCT CACTCAAAGG CGGTAATACG GTTATCCACA    780
GAATCAGGGG ATAACGCAGG AAAGAACATG TGAGCAAAAG GCCAGCAAAA GGCCAGGAAC    840
CGTAAAAAGG CCGCGTTGCT GGCGTTTTTC CATAGGCTCC GCCCCCCTGA CGAGCATCAC    900
AAAAATCGAC GCTCAAGTCA GAGGTGGCGA AACCCGACAG GACTATAAAG ATACCAGGCG    960
TTTCCCCCTG GAAGCTCCCT CGTGCGCTCT CCTGTTCCGA CCCTGCCGCT TACCGGATAC   1020
CTGTCCGCCT TTCTCCCTTC GGGAAGCGTG GCGCTTTCTC AATGCTCACG CTGTAGGTAT   1080
CTCAGTTCGG TGTAGGTCGT TCGCTCCAAG CTGGGCTGTG TGCACGAACC CCCCGTTCAG   1140
CCCGACCGCT GCGCCTTATC CGGTAACTAT CGTCTTGAGT CCAACCCGGT AAGACACGAC   1200
TTATCGCCAC TGGCAGCAGC CACTGGTAAC AGGATTAGCA GAGCGAGGTA TGTAGGCGGT   1260
GCTACAGAGT TCTTGAAGTG GTGGCCTAAC TACGGCTACA CTAGAAGGAC AGTATTTGGT   1320
ATCTGCGCTC TGCTGAAGCC AGTTACCTTC GGAAAAAGAG TTGGTAGCTC TTGATCCGGC   1380
AAACAAACCA CCGCTGGTAG CGGTGGTTTT TTTGTTTGCA AGCAGCAGAT TACGCGCAGA   1440
AAAAAAGGAT CTCAAGAAGA TCCTTTGATC TTTTCTACGG GTCTGACGC TCAGTGGAAC   1500
GAAAACTCAC GTTAAGGGAT TTTGGTCATG AGATTATCAA AAAGGATCTT CACCTAGATC   1560
CTTTTAAATT AAAAATGAAG TTTTAAATCA ATCTAAAGTA TATATGAGTA AACTTGGTCT   1620
GACAGTTACC AATGCTTAAT CAGTGAGGCA CCTATCTCAG CGATCTGTCT ATTTCGTTCA   1680
TCCATAGTTG CCTGACTCCC CGTCGTGTAG ATAACTACGA TACGGGAGGG CTTACCATCT   1740
GGCCCCAGTG CTGCAATGAT ACCGCGAGAC CCACGCTCAC CGGCTCCAGA TTTATCAGCA   1800
ATAAACCAGC CAGCCGGAAG GGCCGAGCGC AGAAGTGGTC CTGCAACTTT ATCCGCCTCC   1860
ATCCAGTCTA TTAATTGTTG CCGGGAAGCT AGAGTAAGTA GTTCGCCAGT TAATAGTTTG   1920
CGCAACGTTG TTGCCATTGC TACAGGCATC GTGGTGTCAC GCTCGTCGTT TGGTATGGCT   1980
TCATTCAGCT CCGGTTCCCA ACGATCAAGG CGAGTTACAT GATCCCCCAT GTTGTGCAAA   2040
AAAGCGGTTA GCTCCTTCGG TCCTCCGATC GTTGTCAGAA GTAAGTTGGC CGCAGTGTTA   2100
TCACTCATGG TTATGGCAGC ACTGCATAAT TCTCTTACTG TCATGCCATC CGTAAGATGC   2160
TTTTCTGTGA CTGGTGAGTA CTCAACCAAG TCATTCTGAG AATAGTGTAT GCGGCGACCG   2220
AGTTGCTCTT GCCCGGCGTC AATACGGGAT AATACCGCGC CACATAGCAG AACTTTAAAA   2280
GTGCTCATCA TTGGAAAACG TTCTTCGGGG CGAAAACTCT CAAGGATCTT ACCGCTGTTG   2340
```

```
AGATCCAGTT CGATGTAACC CACTCGTGCA CCCAACTGAT CTTCAGCATC TTTTACTTTC      2400

ACCAGCGTTT CTGGGTGAGC AAAAACAGGA AGGCAAAATG CCGCAAAAAA GGGAATAAGG      2460

GCGACACGGA AATGTTGAAT ACTCATACTC TTCCTTTTTC AATATTATTG AAGCATTTAT      2520

CAGGGTTATT GTCTCATGAG CGGATACATA TTTGAATGTA TTTAGAAAAA TAAACAAATA      2580

GGGGTTCCGC GCACATTTCC CCGAAAAGTG CCACCTGACG TCTAAGAAAC CATTATTATC      2640

ATGACATTAA CCTATAAAAA TAGGCGTATC ACGAGGCCCT TCGTCTTCA AGAATTCTCA       2700

TGTTTGACAG CTTATCATCG ATAAGCTAGC TTTGGAGATT ATCGTCACTG CAATGCTTCG      2760

CAATATGGCG CAAAATGACC AACAGCGGTT GATTGATCAG GTAGAGGGGG CGCTGTACGA      2820

GGTAAAGCCC GATGCCAGCA TTCCTGACGA CGATACGGAG CTGCTGCGCG ATTACGTAAA      2880

GAAGTTATTG AAGCATCCTC GTCAGTAAAA AGTTAATCTT TTCAACAGCT GTCATAAAGT      2940

TGTCACGGCC GAGACTTATA GTCGCTTTGT TTTTATTTTT TAATGTATTT GTACATGGAG      3000

AAAATAAAGT GAAACAAAGC ACTATTGCAC TGGCACTCTT ACCGTTACTG TTTACCTGTA      3060

AAATCCTGTG ACAAAAGCCC GGATGGCTGA ACAAAGCGAC AAAGACGTCA AAATAAAGTA      3120

AGGAAATACT ACACTCTGGA AGAAATCCAA AAACACAAAG ACTCGAAGTC GACGTTTGGG      3180

ATTGGGTGAT CCTGCACCAT AAAGTATACG ACCTAACTAA ATTCCTCGAA TAATATGGAG      3240

CACCCCGGGG GCGAAGAAGT CCTGAGAGAA CAGGCCGGCG GTGACGGGGG AAGGGAAGGA      3300

GCGACTGAAA ACTTCGAAGA CGTTGGCCAT AGTACCGACG CTCGAGAACT GTCGAAAACG      3360

TACATCATCG GTGAGCTGCA CCCGGACGAT CGTTCTAAAA TCGCGAAACC GTCCGAAACT      3420

CTGATCACTA CCGTTGAATC GAACTCTAGT TGGTGGACTA ACTGGGTTAT CCCTGCGATC      3480

TCTGCTCTGG TTGTAGCGCT GATGTACCGT CTGTACATGG CTGAAGATTA ATGAAAATTA      3540

GTTAAGAGAA TTCGATATCA AGCTTTAGTT CGTCAAGGCT TGGCTAAAGT TGCTTATGTT      3600

TACAAACCTA ACAATACATA TGAACAACAT TTAAGAAAAA GTGAAGCACA AGCGAAAAAA      3660

GAGAAATTAA ATATTTGGAG CGAAGACAAC GCTGATTCAG GTCAATAATG CTCATTGTAA      3720

AAGTGTCACT GCTGCTAGTG GCACTTTTAT AATTTTTAGA TCCTCTACGC CGGACGCATC      3780

GTGGCCGGCA TCACCGGCGC CACAGGTGCG GTTGCTGGCG CCTATATCGC CGACATCACC      3840

GATGGGGAAG ATCGGGCTCG CCACTTCGGG CTCATGAGCG CTTGTTTCGG CGTGGGTATG      3900

GTGGCAGGCC CTTTCGTC                                                   3918

(2) INFORMATION FOR SEQ ID NO: 3:

(i) SEQUENCE CHARACTERISTICS:
        (A) LENGTH: 511 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO: 3:

GTCAGTAAAA AGTTAATCTT TTCAACAGCT GTCATAAAGT TGTCACGGCC GAGACTTATA        60

GTCGCTTTGT TTTTATTTTT TAATGTATTT GTACATGGAG AAAATAAAGT GAAACAAAGC       120

ACTATTGCAC TGGCACTCTT ACCGTTACTG TTTACCCCTG TGACAAAAGC CCGGATCCCC       180

CGGGCTGCAG ATGGCTGAAC AAAGCGACAA AGACGTCAAA TACTACACTC TGGAAGAAAT       240

CCAAAAACAC AAAGACTCGA AGTCGACGTG GGTGATCCTG CACCATAAAG TATACGACCT       300

AACTAAATTC CTCGAAGAGC ACCCCGGGGG CGAAGAAGTC CTGAGAGAAC AGGCCGGCGG       360
```

```
TGACGCGACT GAAAACTTCG AAGACGTTGG CCATAGTACC GACGCTCGAG AACTGTCGAA       420

AACGTACATC ATCGGTGAGC TGCACCCGGA CGATCGTTCT AAAATCGCGA AACCGTCCGA       480

AACTCTGTAA TGAGAATTCG ATATCAAGCT T                                     511
```